United States Patent
Stilwell (10) Patent No.: US 9,439,810 B2
(45) Date of Patent: Sep. 13, 2016

(54) BAREFOOT ORTHOTIC

(71) Applicant: Joseph Gregory Stilwell, Durango, CO (US)

(72) Inventor: Joseph Gregory Stilwell, Durango, CO (US)

(*) Notice: Subject to any disclaimer, the term of this patent is extended or adjusted under 35 U.S.C. 154(b) by 186 days.

(21) Appl. No.: 14/304,940

(22) Filed: Jun. 15, 2014

(65) Prior Publication Data

US 2015/0359682 A1    Dec. 17, 2015

(51) Int. Cl.
*A61F 13/00* (2006.01)
*A61F 13/06* (2006.01)
*A43B 19/00* (2006.01)

(52) U.S. Cl.
CPC ............ *A61F 13/064* (2013.01); *A43B 19/00* (2013.01); *A61F 13/067* (2013.01)

(58) Field of Classification Search
CPC .... A43B 19/00; A61F 13/064; A61F 13/067
USPC ........................................................ 602/66
See application file for complete search history.

(56) References Cited

U.S. PATENT DOCUMENTS

| | | | | |
|---|---|---|---|---|
| 1,417,600 A | * | 5/1922 | Gutmann | A43B 7/1445 36/162 |
| 1,651,285 A | * | 11/1927 | Levick, Jr | A61F 13/065 602/66 |
| 1,952,538 A | * | 3/1934 | Devine | A61F 5/14 36/164 |
| 2,253,429 A | * | 8/1941 | Hess | A43B 7/14 36/180 |
| 2,454,836 A | * | 11/1948 | Rayner | A61F 13/067 602/29 |
| 2,461,047 A | * | 2/1949 | Freedman | A61F 13/067 128/894 |
| 4,510,699 A | * | 4/1985 | Nakamura | A61F 5/14 36/173 |

* cited by examiner

*Primary Examiner* — Kristen Matter (57) ABSTRACT

A barefoot orthotic is a foot support that adheres to the underside of a user's foot and is placed so that it extends longitudinally between the metatarsal head region and the calcaneal plantar tuberosity, and laterally between the lateral midfoot and the medial arch. By using a silicone polymer or other similar material, a barefoot orthotic can self-adhere to the skin of a user's foot. A barefoot orthotic can have a midfoot strike zone surrounding the forward portion of the calcaneal plantar tuberosity, a navicular support, a medial arch support, a forefoot propulsion pad, a lateral forefoot support, a lateral midfoot support, a cuboid support flange, a lateral heel support, and a balance rail extending longitudinally from the midfoot strike zone to the forefoot propulsion pad. Together, these components work to support and align the foot and thereby alleviate symptoms of various foot and leg conditions.

14 Claims, 8 Drawing Sheets

BAREFOOT ORTHOTIC

TECHNICAL FIELD

The invention relates generally to the field of orthotics, and more particularly to a barefoot orthotic.

BACKGROUND

The field of orthotics generally refers to an external device applied to the foot or lower extremity which is used to modify, correct, or support the neuromuscular and skeletal system. Orthotics for the feet usually comprise an insert or custom insole that is added to a shoe or other footwear and redistributes weight, impact forces, and interactions between the foot and the footwear. Traditionally, such devices are customized for the individual user's needs and are transferred between footwear as the user switches shoes.

However, there has been a recent increase in the wearing of footwear in which it is difficult to use traditional orthotics. For example, sandals, five-finger shoes, ballet flats, and similar footwear are extremely difficult to use traditional orthotics therein. Additionally, traditional orthotic inserts can not be utilized when no footwear is worn, as it is difficult to maintain the orthotic in the correct position relative to the foot. This is especially troublesome as the lack of footwear (or otherwise 'minimal footwear') further reduces the support available to a person's foot.

Although many different orthotics are available to support various portions of the foot, there is a need for an orthotic that specifically targets four areas: cuboid support, navicular support, metatarsal support, and medial arch support. These areas of the foot especially benefit from support when no footwear (or minimal footwear) is worn. Therefore, what is needed is an orthotic device that adheres to the user's skin, can be worn with minimal or no footwear, and provides support for three arches of the foot by focusing on supporting the cuboid, navicular, metatarsal, and medial arch areas.

SUMMARY

One embodiment of the present invention comprises a barefoot orthotic that adheres to a user's skin (it can utilize an auto-adhesive material) and so can be worn with minimal or no footwear. The barefoot orthotic is L shaped so as to provide optimum support to the cuboid, navicular, metatarsal and medial arch areas of the foot. The device can comprise a midfoot strike zone, a navicular support, a medial arch support, a forefoot propulsion pad, a lateral forefoot support, a lateral midfoot support, a cuboid support flange, a lateral heel support, and a balance rail. Together, these components work to support and align the foot and thereby alleviate symptoms of various foot and leg conditions.

BRIEF DESCRIPTION OF THE DRAWINGS

The aforementioned and other features and objects of the present invention and the manner of attaining them will become more apparent and the invention itself will be best understood by reference to the following descriptions of a preferred embodiment and other embodiments taken in conjunction with the accompanying drawings, wherein.

DETAILED DESCRIPTION

In the following discussion, numerous specific details are set forth to provide a thorough understanding of the present disclosure. However, those skilled in the art will appreciate that embodiments may be practiced without such specific details. Furthermore, lists and/or examples are often provided and should be interpreted as exemplary only and in no way limiting embodiments to only those examples.

Exemplary embodiments are described below in the accompanying Figures. The following detailed description provides a comprehensive review of the drawing Figures in order to provide a thorough understanding of, and an enabling description for, these embodiments. One having ordinary skill in the art will understand that in some cases well-known structures and functions have not been shown or described in detail to avoid unnecessarily obscuring the description of the embodiments.

Figure 1:
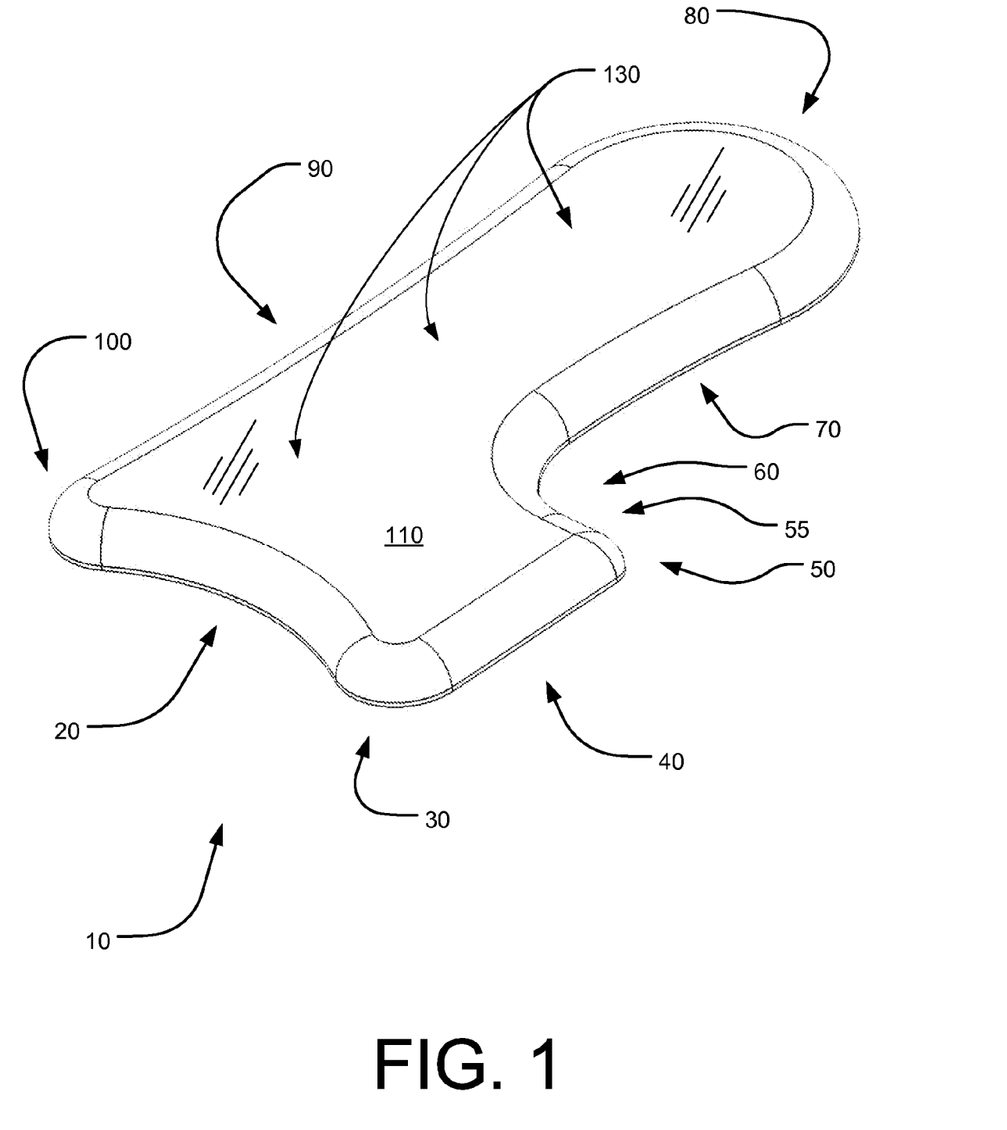
FIG. 1 illustrates a top rear perspective view of an exemplary embodiment of a barefoot orthotic.

Referring now to the drawings, FIG. 1 illustrates a top rear perspective view of an exemplary embodiment of a barefoot orthotic 10. The barefoot orthotic 10 can be made from silicone polymer or any other material that provides similar performance characteristics: is durable, requires minimal thickness, is shock-absorbent, and can be washable and/or reusable. Silicone polymers can also be formulated such that the barefoot orthotic is adhesive and can be applied to a user's skin and remain stuck thereon. Yet the user can remove the barefoot orthotic by simply peeling it off after use. Then, by washing and/or cleaning the barefoot orthotic and letting it air-dry, it regains its adhesive properties and is ready to be reapplied as needed. Alternatively, a separate adhesive can also be utilized. In yet another embodiment, a potassium alum spray can be utilized on those users who have an adhesion problem.

The barefoot orthotic 10 extends longitudinally from the forefoot propulsion pad 80 to the midfoot strike zone 20 and comprises a balance rail 130 region stretching therebetween. The balance rail 130 creates improved proprioception. Support of the medial/lateral columns is achieved as the balance rail 130 provides a center rail of balance for the foot. Furthermore, the balance rail 130 explains pronation and supination control. It is important to note that the balance rail 130 can utilize the same material(s) as the other portions of the barefoot orthotic 10 and can be regarded as an area of the barefoot orthotic rather than a separate component that is attached thereto.

The forefoot propulsion pad 80 area of the barefoot orthotic 10 helps to spread the toes and distribute the user's weight more evenly thereon. This has the added advantage of decreasing stress and pain in the forefoot, potentially decreasing metatarsal stress fractures.

Because the barefoot orthotic 10 can be worn in minimal footwear or barefoot, it is especially useful for runners and/or (pole) walkers, wearers of tight/fashionable/dress shoes, and wearers of footwear that might otherwise show portions of a standard orthotic. The barefoot orthotic 10 can be used in ballet flats, zero-drop shoes, boots, socks, sandals and other minimalist applications. Additionally, the barefoot orthotic 10 can also be used by people in standing occupations as well as those who would otherwise use traditional orthotics.

In the illustrations of FIGS. 1-8, the barefoot orthotic 10 is for a user's "right" foot. The barefoot orthotic 10 for a user's left foot is a mirror image of that shown in FIG. 1. In general, when viewed from above so that the skin-adherence surface 110 is visible, the barefoot orthotic is generally L shaped in the right foot embodiment and a mirror-image of an L in the left foot embodiment. Alternatively, if viewed from above, the right foot embodiment is L shaped; and when viewed from below, the left foot embodiment is L shaped. Additionally, various sizes of barefoot orthotics 10 can be produced so as to fit feet of various sizes.

In FIG. 1, the top portion of the barefoot orthotic 10 is shown highlighting the skin-adherence surface 110. This surface is designed to directly adhere to the skin of the user's foot. The barefoot orthotic 10 can be constructed from self-adhesive material(s) such as a silicone polymer, and/or separate adhesives can be employed to retain the barefoot orthotic 10 in place on a user's foot (see FIG. 8 for placement).

In the embodiment shown in FIG. 1, the midfoot strike zone 20 can be clearly seen. It is shaped so as to decrease the heel strike impact as the wearer runs or walks. Furthermore, the midfoot strike zone 20 supports the origin of the plantar fascia and the anterior to calcaneal tuberosity. The curved heel edge forms to the correct areas of the foot without interfering in the main weight-bearing function of the heel.

Moving from the midfoot strike zone 20 to the medial arch support 90, the barefoot orthotic has a navicular support 100 therebetween. This portion supports the navicular and transitions from the midfoot strike zone 20 to the medial arch support 90. The medial arch support 90 functions to support and strengthen the medial arch area of a person's foot. At the other end of the medial arch support 90 is a forefoot propulsion pad 80. The forefoot propulsion pad 80 supports the metatarsal head region 220 of the foot and helps to spread the toes and evenly distribute the user's weight across this area.

The lateral forefoot support 70 supports the lateral portion of the forefoot 290 opposite the forward portion of the medial arch 240. The lateral forefoot transition 60 extends the barefoot orthotic from the relatively narrow lateral forefoot support 70 to the cuboid support flange 40. This is accomplished by the nearly ninety degree curvature of the lateral forefoot transition 60. In order to terminate and redirect this curvature, two additional components, the lateral midfoot transition 55 and the cuboid support transition 50, reverse the curvature approximately ninety degrees in the opposite direction.

The cuboid support flange 40 widens the barefoot orthotic 10 as it approaches the heel so as to surround the calcaneal plantar tuberosity and provide support to the cuboid. The lateral heel support 30 defines one rear corner of the barefoot orthotic 10 and provides support to the lateral heel area of the foot.

Figure 2:
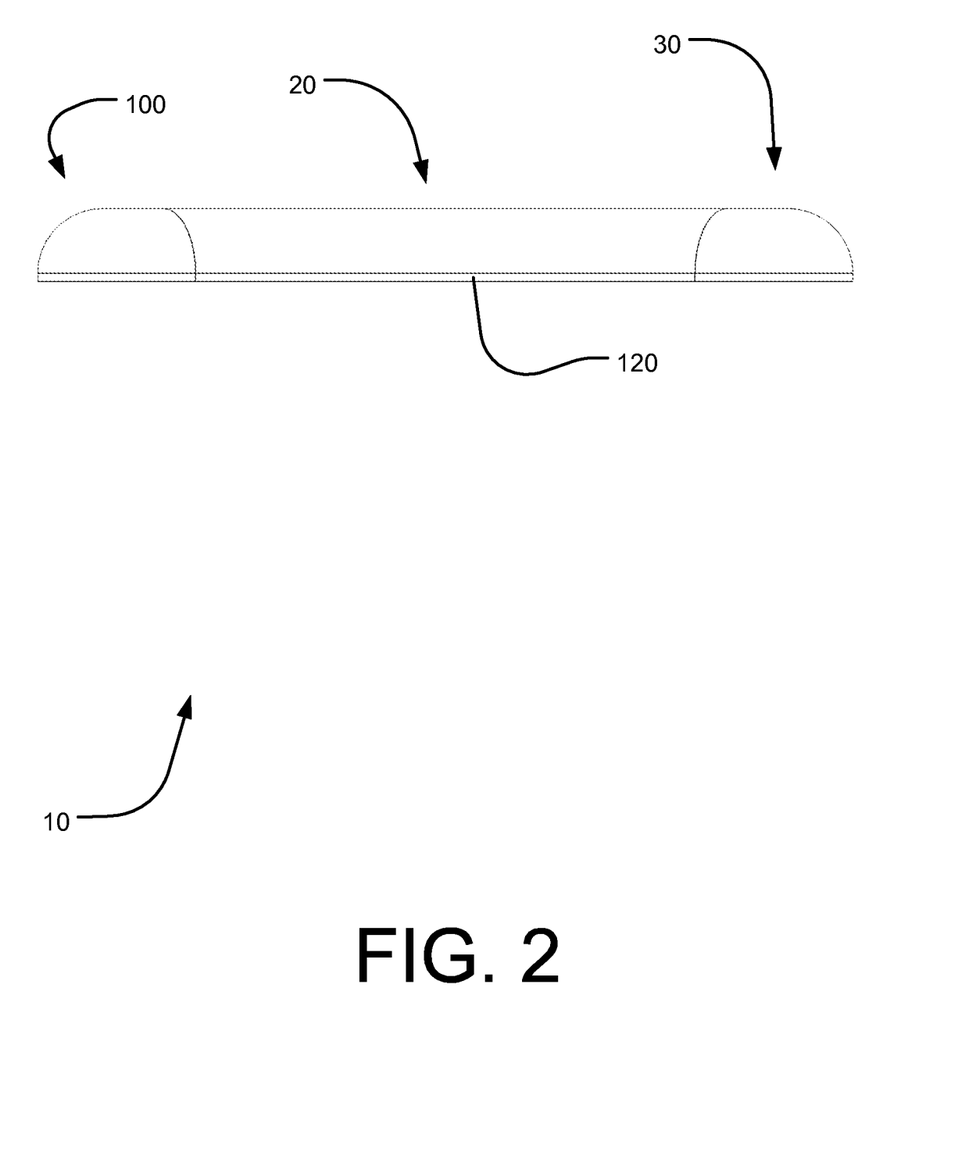
FIG. 2 illustrates a rear elevation view of an exemplary embodiment of a barefoot orthotic.

Extending between the midfoot strike zone 20 and the forefoot propulsion pad 80 is the balance rail 130. The balance rail 130 creates improved proprioception by supporting the medial/lateral columns and providing a center rail of balance for the foot. Together, the above components work to support and align the foot and thereby alleviate symptoms of various foot and leg conditions FIG. 2 illustrates a rear elevation view of an exemplary embodiment of a barefoot orthotic 10. As this is a view from the heel area, the midfoot strike zone 20, the lateral heel support 30, and the navicular support 100 are visible. Also visible is the plantar protective cover 120. The cover 120 can be any sufficiently sturdy material that protects the underside of the barefoot orthotic 10 and can withstand the wear and tear experienced by the barefoot orthotic 10 on a daily basis. In an alternate embodiment, the material comprising the barefoot orthotic 10 is itself able to withstand the wear and tear and so no separate cover 120 material is required; instead, the plantar protective cover 120 simply refers to that surface of the barefoot orthotic 10 opposite the skin-adherence surface 110. Note the generally flat nature of the exemplary embodiment of the barefoot orthotic 10 shown in FIG. 2. The ratio of the width at the heel versus the barefoot orthotic's thickness may vary in other embodiments.

Figure 3:
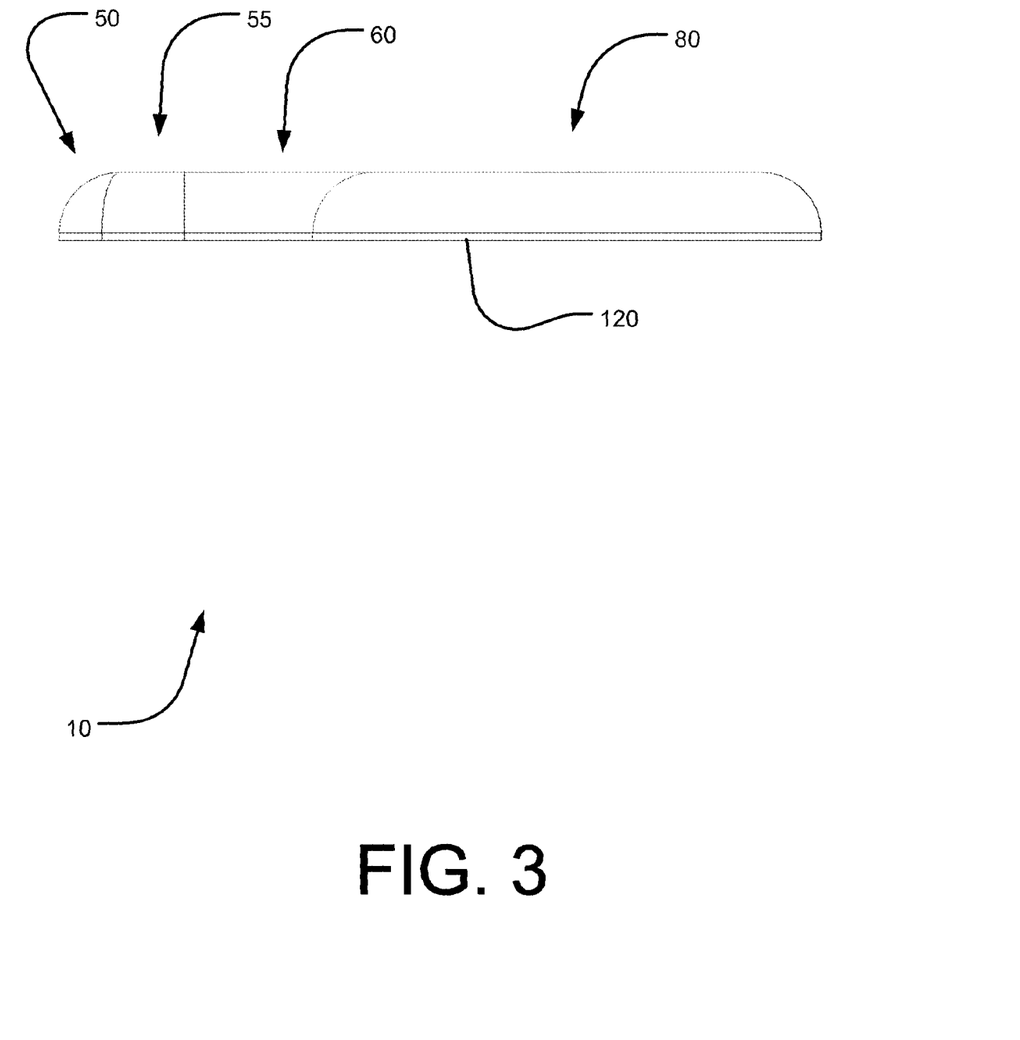
FIG. 3 illustrates a front elevation view of an exemplary embodiment of a barefoot orthotic.

FIG. 3 illustrates a front elevation view of an exemplary embodiment of a barefoot orthotic. In this view, the barefoot orthotic 10 is shown from the forefoot propulsion pad 80 backwards and so the only additional components visible are the lateral forefoot transition 60, the lateral midfoot transition 55, the cuboid support transition 50 and the plantar protective cover 120. The curved shape of the sidewalls of the barefoot orthotic 10 is illustrated as the components transition from the generally flat nature of the protective cover 120 to the skin-adherence surface 110. In the embodiment shown in FIG. 3, the skin-adherence surface 110 has a shape that generally matches that of the plantar protective cover 120, but has a smaller perimeter and so requires the sidewalls to be curved inwards as shown. This inwardly curved shape allows the sidewalls of the barefoot orthotic to compress against the skin of the user's foot during use without bunching up and causing an uncomfortable pressure point. Furthermore, this shape also assists in maintaining the correct placement of the barefoot orthotic on the foot.

Figure 4:
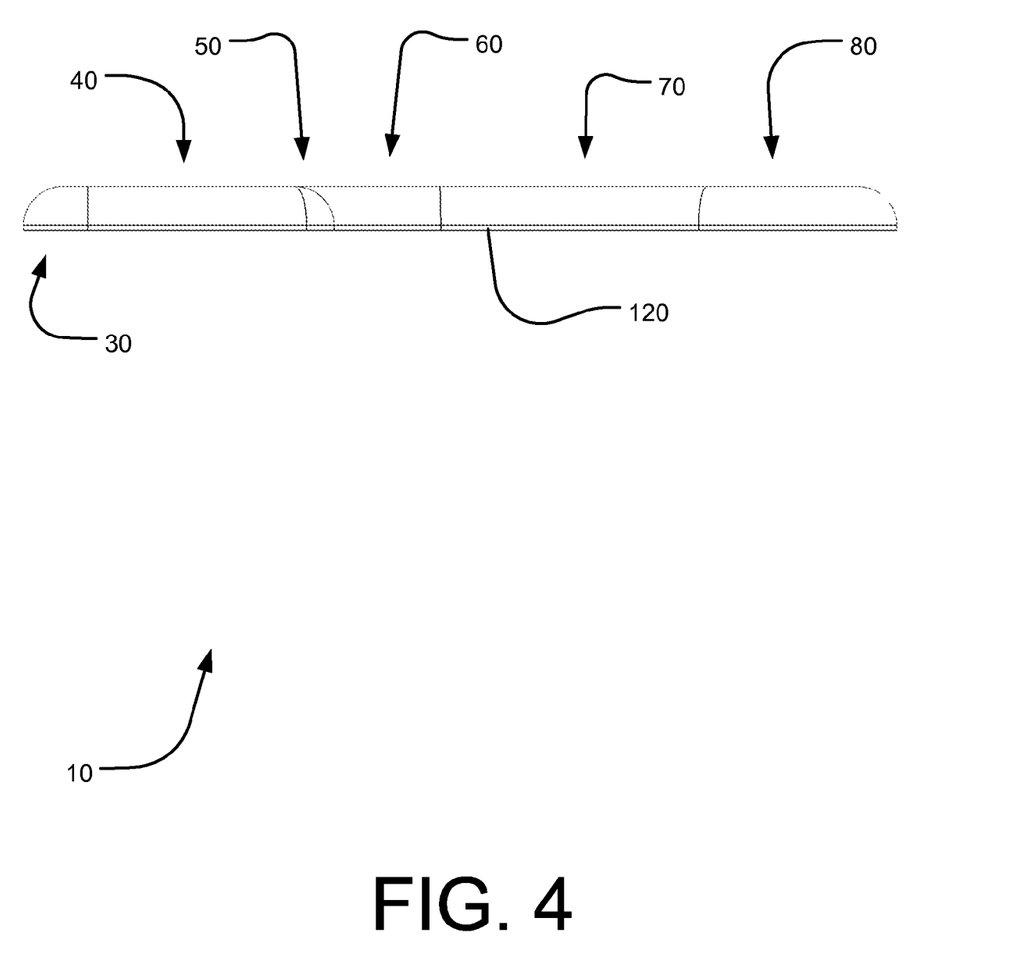
FIG. 4 illustrates a right side elevation view of an exemplary embodiment of a barefoot orthotic.

FIG. 4 illustrates a right side elevation view of an exemplary embodiment of a barefoot orthotic 10. The components visible in this view include the forefoot propulsion pad 80, the lateral forefoot support 70, the lateral forefoot transition 60, the lateral midfoot transition 55, the cuboid support transition 50, the cuboid support flange 40, and the lateral heel support 30 (in additional to the plantar protective cover 120). Note again the inwards curving shape of the sidewall.

Figure 5:
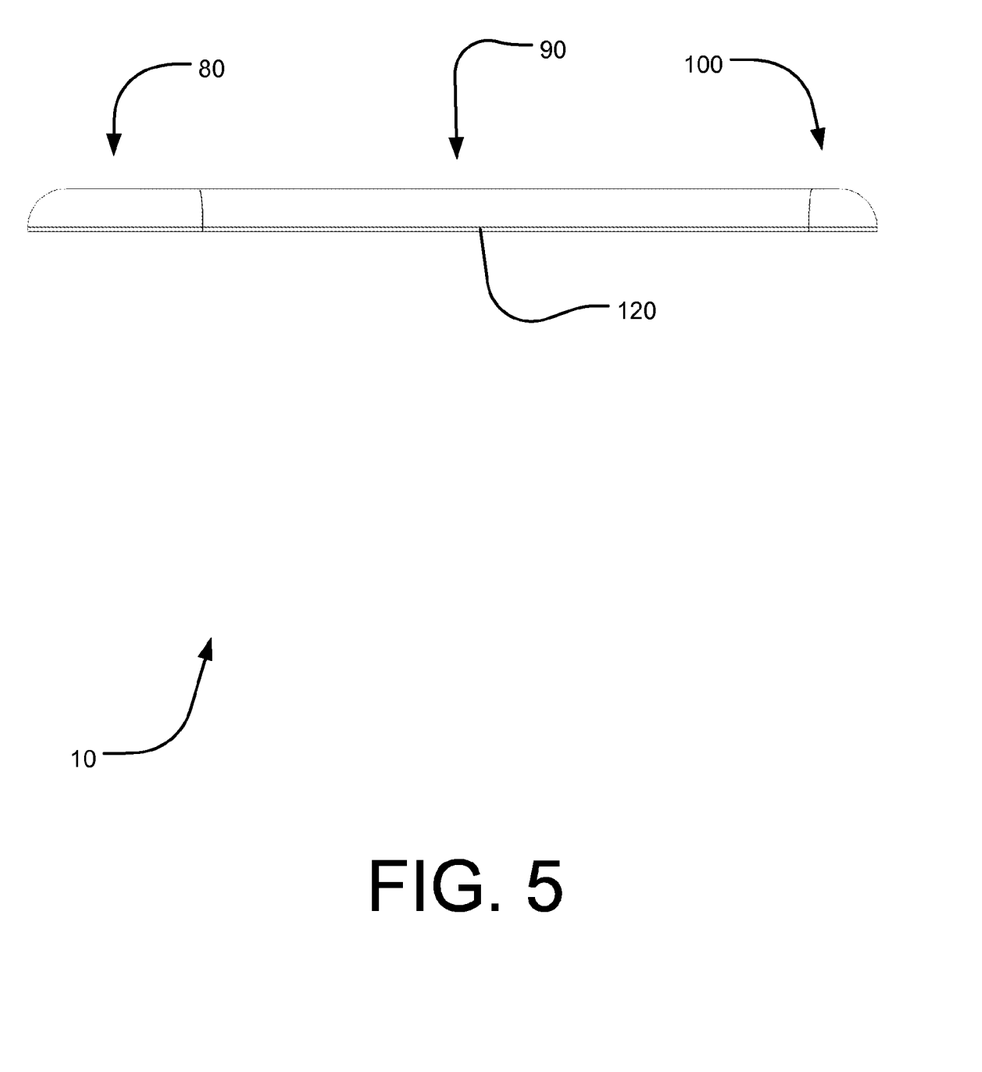
FIG. 5 illustrates a left side elevation view of an exemplary embodiment of a barefoot orthotic.

FIG. 5 illustrates a left side elevation view of an exemplary embodiment of a barefoot orthotic 10 highlighting the forefoot propulsion pad 80, the medial arch support 90, and the navicular support 100.

Figure 6:
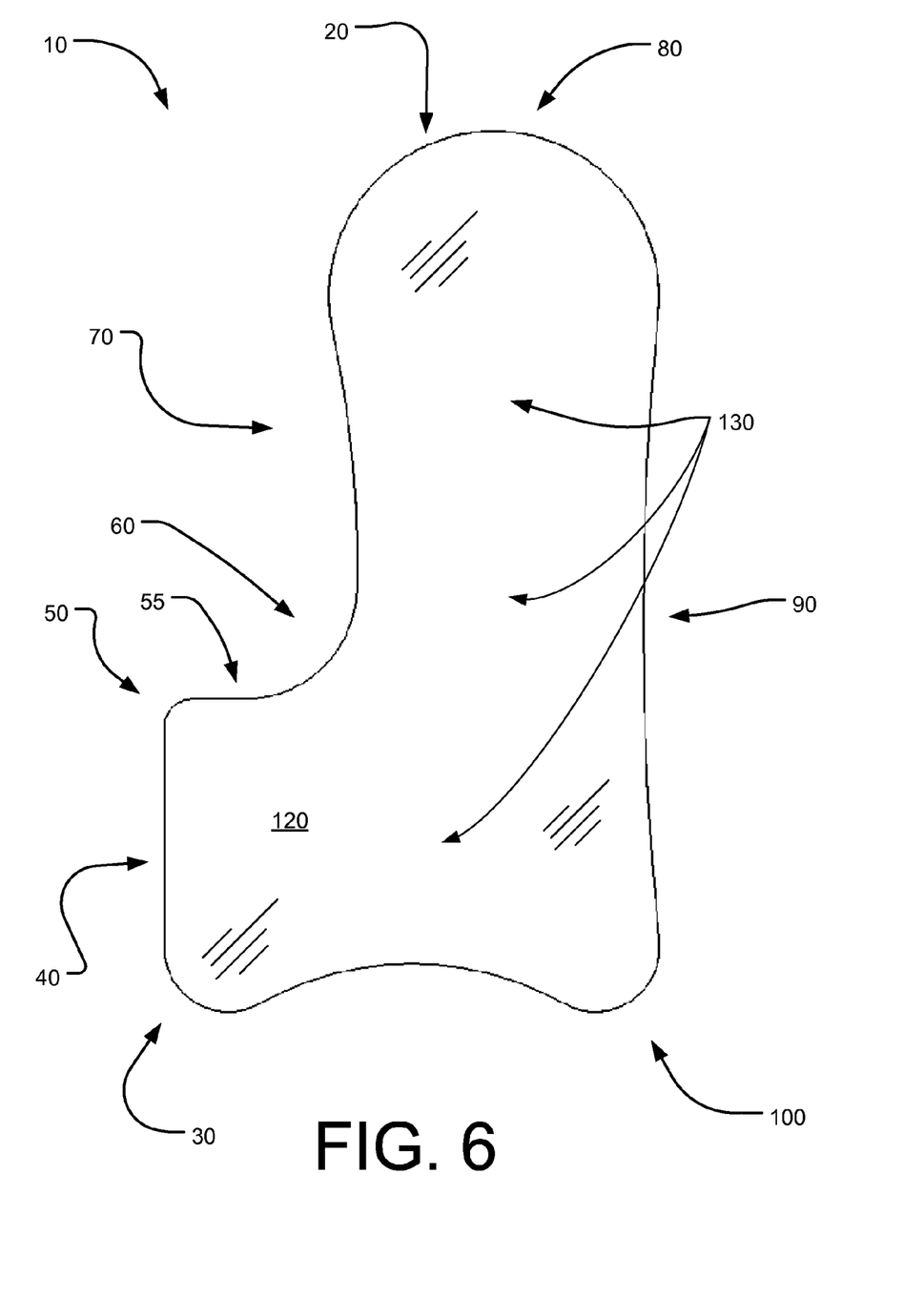
FIG. 6 illustrates a bottom plan view of an exemplary embodiment of a barefoot orthotic.

FIG. 6 illustrates a bottom plan view of an exemplary embodiment of a barefoot orthotic 10. The various components illustrated in FIG. 6 are highlighted throughout the previous drawing figures. Note the generally flat nature of the plantar protective cover 120 and how it comprises a surface opposite the skin-adherence surface 110.

Figure 7:
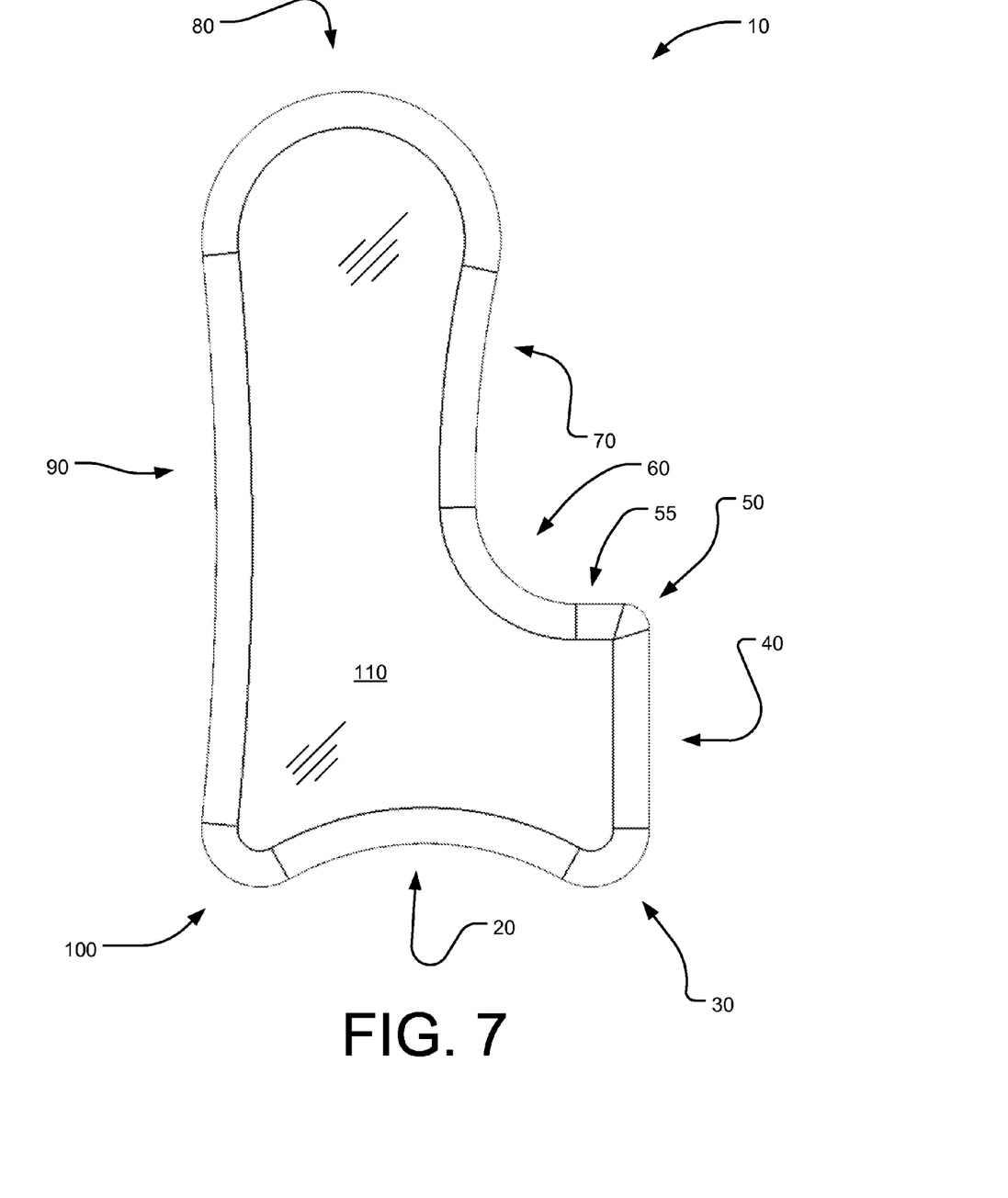
FIG. 7 illustrates a top plan view of an exemplary embodiment of a barefoot orthotic.

FIG. 7 illustrates a top plan view of an exemplary embodiment of a barefoot orthotic 10. The barefoot orthotic 10 shown in FIG. 7 is the same right foot barefoot orthotic 10 illustrated in FIG. 6, it is simply flipped over to illustrate the skin-adherence surface 110 and the curvature of the sidewalls to transition from the plantar protective cover 120 perimeter to the smaller perimeter of the skin-adherence surface 110.

Figure 8:
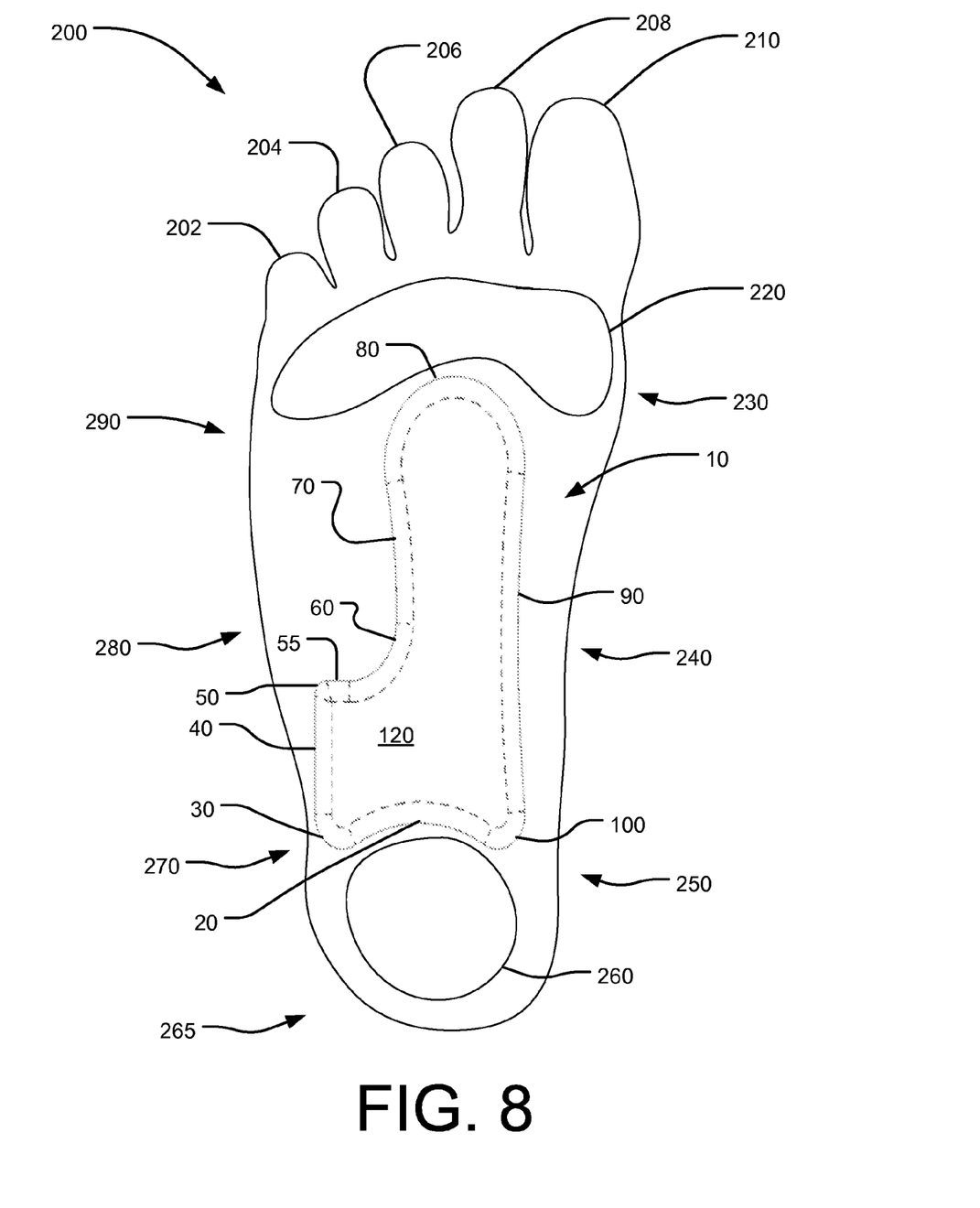
FIG. 8 illustrates a bottom plan view of an exemplary embodiment of a barefoot orthotic emplaced upon a user's foot.

FIG. 8 shows a bottom plan view of an exemplary embodiment of a barefoot orthotic 10 emplaced upon a user's foot 200. The structural delineations are illustrated in broken lines as they are not visible in this view since the bottom surface comprises the plantar protective cover 120 and is generally flat in nature. The user's foot 200 that is illustrated in FIG. 8 is a "right" foot (versus the user's left foot) and comprises the first toe 210 (also known as the big toe, great toe, or hallux), the second toe 208, the third toe 206, the fourth toe 204, the fifth toe 202, the lateral forefoot 290, the lateral midfoot 280, the lateral heel 270, the plantar right heel 265, the calcaneal plantar tuberosity 260, the medial right heel 250, the medial right arch 240, the first metatarsal head 230, and the metatarsal head region 220.

The barefoot orthotic 10 is emplaced generally vertically between the calcaneal plantar tuberosity 260 and the metatarsal head region 220 and generally horizontally between the medial right arch 240 and the lateral midfoot 280. The midfoot strike zone 20 is shaped to surround the forward portion of the calcaneal plantar tuberosity 260 without interfering with the functionality thereof.

Moving from the midfoot strike zone 20 to the medial arch support 90, the barefoot orthotic has a navicular support 100. This portion supports the navicular and transitions from the midfoot strike zone 20 to the proximal end of the medial arch support 90. At the distal end of the medial arch support 90 is a forefoot propulsion pad 80. The forefoot propulsion pad 80 supports the metatarsal head region 220 of the foot and helps to spread the toes and evenly distribute the user's weight across this area.

The lateral forefoot support 70 supports the lateral portion of the forefoot 290 opposite the forward portion of the medial arch 240. The lateral forefoot transition 60 extends the barefoot orthotic from the relatively narrow lateral forefoot support 70 to the cuboid support flange 40. This is accomplished by the nearly ninety degree curvature of the lateral forefoot transition 60. In order to terminate and transition this curvature, two additional components, the lateral midfoot transition 55 and the cuboid support transition 50, reverse the curvature approximately ninety degrees in the opposite direction. The cuboid support flange 40 widens the barefoot orthotic 10 as it approaches the heel so as to surround the calcaneal plantar tuberosity 260 and provide support to the cuboid. The lateral heel support 30 defines one rear corner of the barefoot orthotic 10 and provides support to the lateral heel 270 area of the foot. Together, these components work to support and align the foot and thereby alleviate symptoms of various foot and leg conditions.

While particular embodiments have been described and disclosed in the present application, it is clear that any number of permutations, modifications, or embodiments may be made without departing from the spirit and the scope of this disclosure.

Particular terminology used when describing certain features or aspects of the embodiments should not be taken to imply that the terminology is being redefined herein to be restricted to any specific characteristics, features, or aspects with which that terminology is associated. In general, the terms used in the following claims should not be construed to be limited to the specific embodiments disclosed in the specification, unless the above Detailed Description section explicitly defines such terms. Accordingly, the actual scope of the claims encompasses not only the disclosed embodiments, but also all equivalent ways of practicing or implementing the claimed subject matter.

The above detailed description of the embodiments is not intended to be exhaustive or to limit the invention to the precise embodiment or form disclosed herein or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Any patents, applications and other references that may be listed in accompanying or subsequent filing papers, are incorporated herein by reference. Aspects of the invention can be modified, if necessary, to employ the systems, functions, and concepts of the various references to provide yet further embodiments of the invention.

In light of the above "Detailed Description," the Inventor may make changes to the invention. While the detailed description outlines possible embodiments of the invention and discloses the best mode contemplated, no matter how detailed the above appears in text, the invention may be practiced in a myriad of ways. Thus, implementation details may vary considerably while still being encompassed by the spirit of the invention as disclosed by the inventor. As discussed herein, specific terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

The above specification, examples and data provide a description of the structure and use of exemplary implementations of the described articles of manufacture and methods. It is important to note that many implementations can be made without departing from the spirit and scope of the invention.

What is claimed is:

1. An orthotic, comprising:
 a flexible sole having an upper surface that is adapted to adhere to a user's foot with an adhesive, the flexible sole comprising;
 a midfoot strike zone portion that is generally concave in shape and that is configured to support the origin of the plantar fascia and anteriorly border the user's calcaneus bone to allow the bone to move relative to the orthotic and perform the calcaneus bone's weight-bearing function;
 a balance rail portion extending longitudinally from the midfoot strike zone portion towards the user's metatarsal head region, the balance rail portion being configured to support the user's central medial and lateral columns;
 a forefoot propulsion pad portion that is convex in shape that is configured to support the user's central metatarsal head region and spread the user's toes; and
 a cuboid support flange extending laterally towards the outside of the user's foot from the midfoot strike zone portion, when in use, the cuboid support flange configured to surround the calcaneal plantar tuberosity and provide support to the user's cuboid bone.

2. The orthotic of claim 1, wherein the flexible sole has a generally uniform thickness.

3. The orthotic of claim 2, wherein the flexible sole is generally L-shaped.

4. The orthotic of claim 2, wherein the flexible sole comprises an elastomer.

5. The orthotic of claim 4, wherein the elastomer is comprised of a reusable adhering material that regains its adhesive properties after washing.

6. The orthotic of claim 2, wherein the flexible sole is disposable and not intended to be reused.

7. An orthotic, comprising:
a flexible sole having a generally uniform thickness and an upper adhesive surface that is adapted to adhere to a user's foot with an adhesive, the flexible sole comprising;
a midfoot strike zone portion that is generally concave in shape and that is configured to support the origin of the plantar fascia and anteriorly border the user's calcaneus bone to allow the bone to move relative to the orthotic and perform the calcaneus bone's weight-bearing function;
a balance rail portion extending longitudinally from the midfoot strike zone portion towards the user's metatarsal head region, the balance rail portion being configured to support the user's central medial and lateral columns;
a forefoot propulsion pad portion that is convex in shape that is configured to support the user's central metatarsal head region and spread the user's toes; and
a cuboid support flange extending laterally towards the outside of the user's foot from the midfoot strike zone portion, when in use, the cuboid support flange configured to surround the calcaneal plantar tuberosity and provide support to the user's cuboid bone.

8. The orthotic of claim 7, wherein the flexible sole has generally a L-shape.

9. The orthotic of claim 7, wherein the flexible sole comprises an elastomer.

10. The orthotic of claim 9, wherein the elastomer is comprised of a reusable adhering material that regains its adhesive properties after washing.

11. The orthotic of claim 7, wherein the flexible sole is disposable and not intended to be reused.

12. An orthotic, comprising:
a generally L-shaped flexible sole having a generally uniform thickness and an upper adhesive surface that is adapted to adhere to a user's foot with an adhesive, the flexible sole comprising;
a midfoot strike zone portion that is generally concave in shape and that is configured to support the origin of the plantar fascia and anteriorly border the user's calcaneus bone to allow the bone to move relative to the orthotic and perform the calcaneus bone's weight-bearing function;
a balance rail portion extending longitudinally from the midfoot strike zone portion towards the user's metatarsal head region, the balance rail portion being configured to support the user's central medial and lateral columns;
a forefoot propulsion pad portion that is convex in shape that is configured to support the user's central metatarsal head region and spread the user's toes; and
a cuboid support flange extending laterally towards the outside of the user's foot from the midfoot strike zone portion, when in use, the cuboid support flange configured to surround the calcaneal plantar tuberosity and provide support to the user's cuboid bone.

13. The orthotic of claim 12, wherein the flexible sole comprises an elastomer.

14. The orthotic of claim 13, wherein the elastomer is comprised of a reusable adhering material that regains its adhesive properties after washing.

* * * * *